(12) United States Patent
Stirk et al.

(10) Patent No.: US 11,236,066 B2
(45) Date of Patent: Feb. 1, 2022

(54) CRYSTALLINE FORMS OF NIRAPARIB TOSYLATE

(71) Applicant: Apotex Inc., Toronto (CA)

(72) Inventors: Alexander J. Stirk, Cambridge (CA); Fabio E. S. Souza, Mississauga (CA); Avedis Karadeolian, Cambridge (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 21 days.

(21) Appl. No.: 16/928,127

(22) Filed: Jul. 14, 2020

(65) Prior Publication Data

US 2021/0017151 A1  Jan. 21, 2021

Related U.S. Application Data

(60) Provisional application No. 62/874,699, filed on Jul. 16, 2019.

(51) Int. Cl.
*C07D 401/10* (2006.01)
*A61K 9/48* (2006.01)

(52) U.S. Cl.
CPC .............. *C07D 401/10* (2013.01); *A61K 9/48* (2013.01); *C07B 2200/13* (2013.01)

(58) Field of Classification Search
CPC .......................... C07D 401/10; C07B 2200/13
See application file for complete search history.

(56) References Cited

U.S. PATENT DOCUMENTS

| | | |
|---|---|---|
| 2020/0016142 A1 | 1/2020 | McGurk et al. |
| 2020/0017462 A1 | 1/2020 | Wu et al. |

FOREIGN PATENT DOCUMENTS

| | | |
|---|---|---|
| CN | 108530425 A | 9/2018 |
| WO | 2018183349 A1 | 10/2018 |
| WO | 2018183354 A1 | 10/2018 |
| WO | 2020072860 A1 | 4/2020 |

OTHER PUBLICATIONS

Bernstein, "Polymorphism in Molecular Crystals", Oxford University Press, New York, 2002, pp. 9-10.
Pei, "Crystalline Form of Niraparib Tosylate", Apotex Pharmachem (Tianjin) Inc., 2018, 8 pages.
Porter, "Coating of Pharmaceutical Dosage Forms", Remington the Science and Practice of Pharmacy, Lippincott Williams & Wilkins, Baltimore, 2006, Chapter 46, pp. 929-938.
Rudnic et al., "Oral Solid Dosage Forms", Remington the Science and Practice of Pharmacy, Lippincott Williams & Wilkins, Baltimore, 2006, Chapter 45, pp. 889-928.
Anonymous, "Solid State Forms of 2-[4-[(3S)-Piperidin-3-YL]Phenyl]-2H-Indazole-7-Carboxamide4-Methylbenzenesulfonate", IP.com, 2018, 6 pages.
"Zejula Assessment Report", European Medicines Agency, London, 2017, pp. 1-122.

*Primary Examiner* — Emily A Bernhardt
(74) *Attorney, Agent, or Firm* — The Webb Law Firm

(57) ABSTRACT

The present invention provides novel crystalline forms of niraparib tosylate. Specific crystalline forms provided by the present invention include niraparib tosylate Form APO-I, a co-crystal of niraparib tosylate and urea, and niraparib tosylate Form APO-II, a co-crystal of niraparib tosylate and oxalic acid. Also provided are pharmaceutical compositions including the niraparib tosylate crystalline forms, and the use of these forms in treatment or prevention of conditions which can be ameliorated by the inhibition of poly(ADP-ribose) polymerase (PARP), in particular certain forms of cancer.

20 Claims, 2 Drawing Sheets

CRYSTALLINE FORMS OF NIRAPARIB TOSYLATE

CROSS-REFERENCE TO RELATED APPLICATION

This application claims priority to U.S. Provisional Patent Application No. 62/874,699, filed Jul. 16, 2019, the disclosure of which is hereby incorporated by reference in its entirety.

TECHNICAL FIELD

The present invention is directed to novel crystalline forms of niraparib tosylate, processes for the preparation thereof, pharmaceutical compositions containing these forms, and their use for the treatment or prevention of conditions which can be ameliorated by the inhibition of poly(ADP-ribose) polymerase (PARP), including certain forms of cancer.

BACKGROUND

Niraparib (1), or 2-{4-[(3S)-piperidin-3-yl]phenyl}-2H-indazole 7-carboxamide, in the form of its 4-methylbenzenesulfonate (tosylate) salt monohydrate (1:1:1), exhibits activity as a poly(ADP-ribose) polymerase inhibitor, and is the active ingredient in ZEJULA®, which is indicated for the maintenance treatment of adult patients with recurrent epithelial ovarian, fallopian tube, or primary peritoneal cancer who are in a complete or partial response to platinum-based chemotherapy.

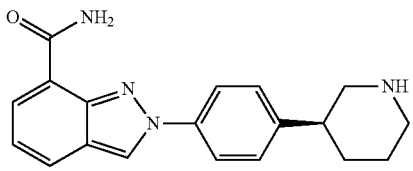

(1)

WO 2018/183354 A1 discloses crystalline Forms I-III of niraparib tosylate. Monohydrate crystalline Form I is described as a non-hygroscopic solid form having suitable solubility properties, as well as favourable physical and chemical stability. Crystalline Form II is characterized as a non-stoichiometric hydrate and anhydrous crystalline Form III is designated as a very hygroscopic solid showing a 15.8% weight gain up to 95% relative humidity (RH) in dynamic vapour sorption (DVS) studies.

Further crystalline forms of niraparib tosylate are described in, for example, CN108530425 A, *IP.com Journal* 2018, 18 (1B), 1-7 and *IP.com Journal* 2018, 18 (3A), 1-5.

According to the European CHMP Assessment Report for ZEJULA® (EMEA/H/C/004249/0000), the drug substance niraparib tosylate in the approved drug product is a non-hygroscopic monohydrate form, which is believed to correspond with crystalline Form I of WO 2018/183354 A1. In the report, the drug substance is further described as having low, pH-independent aqueous solubility but high permeability, placing Niraparib tosylate monohydrate in Class II of the Biopharmaceutics Classification System (BCS). Generally, in the case of solid oral dosage forms of Class II drug substances, the limiting factor controlling drug absorption and bioavailability is adequate solubilization of the drug in the aqueous environment of the gastrointestinal tract. As such, improvements in aqueous solubility of the drug substance can be directly correlated with improved drug effectiveness.

Approaches to improving the solubility of a drug substance include, for example, particle size reduction techniques, dispersion of the drug substance onto an inert carrier, and formulation of the drug substance together with solubilizing excipients. However, WO 2018/183349 A1, which is directed to pharmaceutical capsule compositions of niraparib tosylate, including compositions comprising crystalline Form I of niraparib tosylate, states that there are multiple challenges associated with niraparib tosylate due to its cohesive nature. Cohesive powders, such as crystalline Form I of niraparib tosylate, have a tendency to develop agglomerates and lumps during formulation processing operations, such as mixing and blending, which can lead to problems with flowability and content uniformity of dosage units. The cohesiveness of a powder and the tendency to form agglomerates can also increase as particle size is reduced. Further, as noted in WO 2018/183349 A1, applying strong mechanical agitation processes to a cohesive solid such as crystalline Form I of niraparib tosylate, such as milling, can induce the development of static charge in the material, which can further reduce powder flow properties. Thus, although niraparib tosylate monohydrate exhibits poor aqueous solubility, particle size reduction techniques comprising vigorous mechanical agitation such as milling and spray drying may not be suitable techniques to address the problems with this crystalline form.

One important measure of the solubility of a drug substance is intrinsic dissolution rate (IDR), which is the dissolution rate of a substance under constant surface area conditions. For low solubility substances such as niraparib tosylate that are classified as BCS Class II, higher IDR values can correlate with higher bioavailability following administration. Prediction of the solubility and IDR of an as yet undiscovered crystalline form of a substance is currently not possible.

Different crystalline forms of the same compound may have different packing, thermodynamic, spectroscopic, kinetic, surface, and mechanical properties. For example, different crystalline forms may have different stability properties. A particular crystalline form may be more sensitive to heat, relative humidity (RH) and/or light. Alternatively or additionally, a particular crystalline form may have different compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Additionally, the particular solubility characteristics of a given crystalline form in relation to undesired impurities can result in differences in the chemical purity of different crystalline forms upon isolation. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more cohesive, more resistant to flow, less capable of dispersing static charge or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Therefore, there exists a need for novel crystalline forms of niraparib tosylate for use in providing improved drug products containing niraparib tosylate and their manufacture.

SUMMARY OF THE INVENTION

The crystalline forms of the present invention comprise niraparib tosylate co-crystallized with an equimolar amount of either urea or oxalic acid, each co-former having an established safety record. Owing to the use of co-formers with an established safety record, it is expected that both urea and oxalic acid can safely be used in materials intended for use in the preparation of pharmaceutical compositions intended for administration to humans or animals. Further, the crystalline forms of the present invention exhibit advantageous properties, for example higher IDR values and/or lower chargeability in comparison to crystalline Form I niraparib tosylate described in WO 2018/183354 A1, which is believed to be the form of niraparib tosylate used in ZEJULA® tablets. Thus, the crystalline forms of the present invention offer opportunities to address problems associated with the formulation and use of niraparib tosylate as a drug product, such as low solubility and poor flowability.

In addition, the processes for the manufacture of the niraparib tosylate crystalline forms of the present invention are efficient and substantially solvent-free processes.

Accordingly, in a first aspect of the present invention, there is provided a crystalline form of niraparib tosylate comprising niraparib tosylate and urea. In a preferred embodiment of the first aspect, the molar ratio of niraparib tosylate to urea is between approximately 1:0.75 and 1:1.25. In a more preferred embodiment of the first aspect, the molar ratio of niraparib tosylate to urea is approximately 1:1.

In a second aspect of the present invention, there is provided a crystalline form of niraparib tosylate, APO-I, comprising niraparib tosylate and urea, characterized by a PXRD diffractogram comprising peaks, expressed in degrees 2θ (±0.2°), at 5.2°, 6.6° and 8.4°. In a preferred embodiment of the second aspect, the PXRD diffractogram further comprises at least three peaks, expressed in degrees 2θ (±0.2°), selected from the group consisting of: 12.2°, 14.3°, 14.8°, 15.5°, 18.5° and 21.8°. In a further preferred embodiment of the second aspect, the PXRD diffractogram further comprises peaks, expressed in degrees 2θ (±0.2°), at 12.2°, 14.3°, 14.8°, 15.5°, 18.5° and 21.8°. Preferably, the crystalline form of the second aspect of the invention provides a PXRD diffractogram comprising peaks in substantially the same positions (±0.2° 2θ) as those shown in FIG. 1. In a further preferred embodiment of the second aspect, the molar ratio of niraparib tosylate to urea is approximately 1:1.

In a third aspect of the present invention, there is provided a crystalline form of niraparib tosylate comprising niraparib tosylate and oxalic acid. Preferably, in the crystalline form of the third aspect, the molar ratio of niraparib tosylate to oxalic acid is between approximately 1:0.75 and 1:1.25. Most preferably, the molar ratio of niraparib tosylate to oxalic acid is approximately 1:1.

In a fourth aspect of the present invention, there is provided a crystalline form of niraparib tosylate, APO-II, comprising niraparib tosylate and oxalic acid, characterized by a PXRD diffractogram comprising peaks, expressed in degrees 2θ (±0.2°), at 5.8°, 7.6° and 10.6°. In a preferred embodiment of the fourth aspect, the PXRD diffractogram further comprises at least three peaks, expressed in degrees 2θ (±0.2°), selected from the group consisting of: 12.8°, 14.2°, 15.2°, 16.7°, 17.3° and 20.9°. In a further preferred embodiment of the fourth aspect, the PXRD diffractogram further comprises peaks, expressed in degrees 2θ (±0.2°), 12.8°, 14.2°, 15.2°, 16.7°, 17.3° and 20.9°. Preferably, the crystalline form of the fourth aspect of the invention provides a PXRD diffractogram comprising peaks in substantially the same positions (±0.2° 2θ) as those shown in FIG. 2. In a further preferred embodiment of the fourth aspect, the molar ratio of niraparib tosylate to oxalic acid is approximately 1:1.

In a fifth aspect of the present invention, there is provided a pharmaceutical composition comprising a crystalline form of niraparib tosylate according to any one of the first, second, third or fourth aspects of the invention, and one or more pharmaceutically acceptable excipients. Preferably, the pharmaceutical composition is in the form of a solid dosage form. Most preferably, the pharmaceutical composition is a capsule.

In a sixth aspect of the present invention, there is provided a use of a crystalline form of niraparib tosylate according to any one of the first, second, third or fourth aspects of the invention, or the pharmaceutical composition of the fifth aspect of the invention, in the treatment of conditions which can be ameliorated by the inhibition of poly(ADP-ribose) polymerase (PARP). In a preferred embodiment of the sixth aspect, the condition which can be ameliorated by the inhibition of poly(ADP-ribose) polymerase (PARP) is cancer. In a further preferred embodiment of the sixth aspect, the cancer is selected from the group consisting of epithelial ovarian, fallopian tube, primary peritoneal and combinations thereof. In a further preferred embodiment of the sixth aspect, the cancer is a recurrent cancer that has partially or completely responded to previous treatment with a platinum-based chemotherapy. Also provided is the use of the crystalline form of niraparib tosylate according to any one of the first, second, third or fourth aspects of the invention, or the pharmaceutical composition of the fifth aspect of the invention, in the treatment of a cancer that is selected from the group consisting of epithelial ovarian, fallopian tube, primary peritoneal and combinations thereof.

In a seventh aspect of the present invention, there is provided a process for the preparation of the crystalline form of niraparib tosylate of the first or second aspects of the invention, comprising mixing together a solid phase of niraparib tosylate and a solid phase of urea for a suitable time to afford the crystalline form of niraparib tosylate. In a preferred embodiment of the seventh aspect, mixing is conducted in the presence of a limited amount of a suitable solvent so as to maintain a solid phase throughout mixing. In a further preferred embodiment of the seventh aspect, the suitable solvent is acetonitrile. In a further preferred embodiment of the seventh aspect, the amount of suitable solvent used in the process is between approximately 5 wt % and approximately 20 wt %. Preferably, the amount of suitable solvent used is between approximately 10 wt % and approximately 15 wt %. In a further preferred embodiment of the seventh aspect, the molar ratio of niraparib tosylate to urea used in the process is approximately 1:1. In a further preferred embodiment of the seventh aspect, the mixing comprises grinding.

In an eighth aspect of the present invention, there is provided a process for the preparation of the crystalline form of niraparib tosylate of the third or fourth aspects of the invention, comprising mixing together a solid phase of niraparib tosylate and a solid phase of oxalic acid for a suitable time to afford the crystalline form of niraparib tosylate. In a preferred embodiment of the eighth aspect, mixing is conducted in the presence of a limited amount of a suitable solvent so as to maintain a solid phase throughout mixing. In a further preferred embodiment of the eighth aspect, the suitable solvent is methanol. In a further preferred embodiment of the eighth aspect, the amount of suitable solvent used in the process is between approximately 5 wt % and approximately 20 wt %. Preferably, the amount of suitable solvent used is between approximately 10 wt % and approximately 15 wt %. In a further preferred embodiment of the eighth aspect, the molar ratio of niraparib tosylate to oxalic acid used in the process is approximately 1:1. In a further preferred embodiment of the eighth aspect, the mixing comprises grinding.

In a ninth aspect of the present invention, there is provided a method for treating cancer selected from the group consisting of epithelial ovarian, fallopian tube, primary peritoneal and combinations thereof comprising administering an effective amount of the crystalline form of niraparib tosylate according to any one of first, second, third or fourth aspects of the invention, or the pharmaceutical composition of the fifth aspect of the invention.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The present invention provides niraparib tosylate crystalline forms, including multiple-component crystalline forms comprised of niraparib tosylate and a co-former having an established safety record selected from urea and oxalic acid. Importantly, with respect to the use of these crystalline forms, urea and oxalic acid are water soluble compounds which occur naturally in the human body and/or in food products. Further, urea is included in the U.S. Food & Drug Administration's (FDA's) Generally Recognized as Safe (GRAS) list and the Inactive Ingredient Database (IID). The GRAS list is an inventory of substances generally recognized by the FDA as having been adequately shown to be safe under the conditions of intended use. The IID list provides information on inactive ingredients present in FDA-approved drug products. Once an inactive ingredient has appeared in an approved drug product, the inactive ingredient is not considered new, and may require a less extensive review the next time it is included in a new drug product. Oxalic acid, which can have harmful effects at high doses (e.g. 600 mg/kg body weight), has nonetheless been used as a pharmaceutically acceptable counterion in FDA-approved drug products MOVANTIK® and LEXAPRO®. As such, it is expected that these co-formers can safely be used in materials intended for use in the preparation of pharmaceutical compositions intended for administration to humans or animals.

Further, the multiple-component crystalline forms of the present invention have physical attributes which address problems, such as poor water solubility and poor flowability associated with crystalline Form I of niraparib tosylate, which is believed to be the form of niraparib tosylate used in ZEJULA® capsules. In comparison to crystalline Form I of niraparib tosylate, it is exemplified in the present invention that Form APO-I exhibits lower chargeability whereas Form APO-II exhibits higher IDR values.

The niraparib tosylate crystalline forms of the present invention exhibit differences in properties when compared to known crystalline forms of niraparib tosylate. Depending on the specific crystalline form of the invention used, properties that differ between the invention and known crystalline forms of niraparib tosylate include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, cohesiveness, compactibility, tableting, handling, flow, and blending.

Additionally, the processes for the manufacture of the niraparib tosylate crystalline forms of the present invention are efficient, high yielding and 'green' owing to the use of marginal amounts of solvent.

Figure 1:
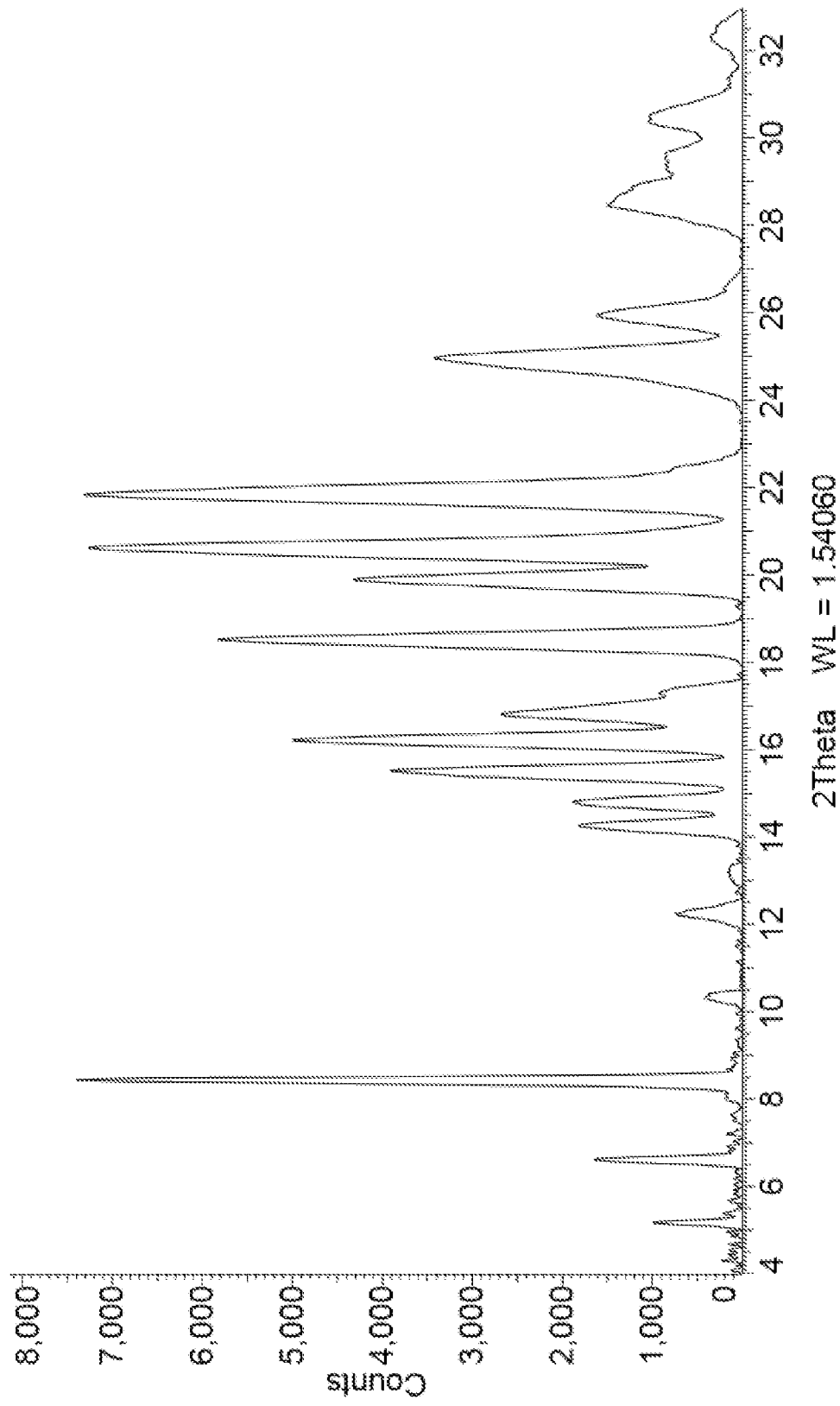
FIG. 1 is a representative PXRD diffractogram of niraparib tosylate Form APO-I as prepared in Example 1.
Figure 2:
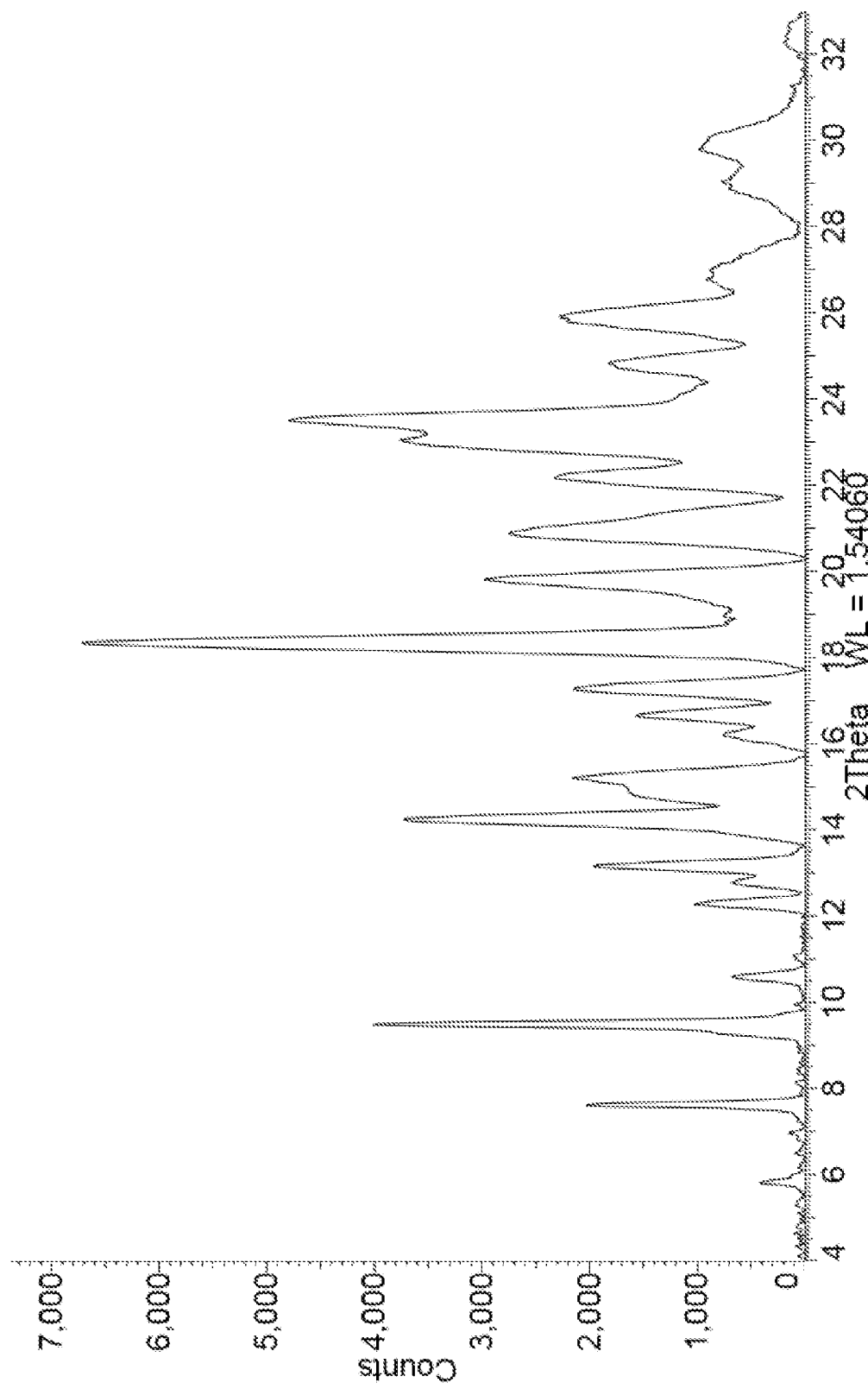
FIG. 2 is a is a representative PXRD diffractogram of niraparib tosylate Form APO-II as prepared in Example 2.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractograms provided in FIGS. 1 and 2. Thus, differences in relative peak intensities between peaks in a PXRD diffractogram for a given crystalline form may be observed when compared to the relative peak intensities of the peaks in the representative PXRD diffractograms of FIGS. 1 and 2. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1 and 2, it is understood that individual peak positions may vary between ±0.2° 2θ from the values observed in the representative PXRD diffractograms provided in FIGS. 1 and 2 for the crystalline forms of the invention, or listed in Tables 1 and 2. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 and 2. Thus, the PXRD diffractogram of the crystalline forms of the present invention may, in some circumstances, display the same relative peak positions as observed in the representative PXRD diffractograms provided in FIGS. 1 and 2, with the exception that each peak is offset in the same direction, and by approximately the same amount, such that the overall PXRD diffractogram is substantially the same in appearance as the PXRD diffractograms of FIGS. 1 and 2, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 and 2.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms of niraparib tosylate. Single-component forms of niraparib tosylate consist solely of niraparib tosylate in the repeating unit of the crystal lattice. Multiple-component forms of niraparib tosylate include co-crystals, salts, and solvates of niraparib tosylate wherein a co-former, counterion or solvent is also incorporated into the crystal lattice.

As used herein, the term 'co-crystal' refers to a multiple-component crystalline form containing both niraparib tosylate and a co-former that is solid under ambient conditions.

As used herein, the term "room temperature" refers to a temperature in the range of 20° C. to 25° C.

Unless defined otherwise herein, the term "approximately", when used in reference to molar ratios, allows for a variance of plus or minus 10%.

It should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, when referring to the amount of suitable solvent, the term "weight percentage" (wt %) refers to the ratio: weight solvent/(weight solvent+weight niraparib tosylate+weight co-former), expressed as a percentage, wherein co-former refers to urea or oxalic acid, as the case may be.

As used herein, the term 'niraparib tosylate' refers to the salt niraparib monotosylate or 2-{4-[(3S)-piperidin-3-yl]phenyl}-2H-indazole 7-carboxamide 4-methylbenzenesulfonate.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of niraparib tosylate, niraparib tosylate Form APO-I, comprising niraparib tosylate and urea. Preferably, in niraparib tosylate Form APO-I, the molar ratio of niraparib tosylate to urea is approximately 1:1.

Niraparib tosylate Form APO-I can be characterized by a PXRD diffractogram comprising, among other peaks, characteristic peaks, expressed in degrees 2θ (±0.2°), at 5.2°, 6.6° and 8.4°. Preferably, the PXRD diffractogram further comprises at least three peaks, expressed in degrees 2θ (±0.2°), selected from the group consisting of 12.2°, 14.3°, 14.8°, 15.5°, 18.5° and 21.8°. More preferably, the PXRD diffractogram further comprises peaks, expressed in degrees 2θ (±0.2°), at 12.2°, 14.3°, 14.8°, 15.5°, 18.5° and 21.8°.

An illustrative PXRD diffractogram of niraparib tosylate Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the niraparib tosylate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of niraparib tosylate Form APO-I from FIG. 1

| Angle (2θ) | Relative intensity (%) |
| --- | --- |
| 5.17 | 9.4 |
| 6.61 | 20.3 |
| 8.44 | 100.0 |
| 10.31 | 5.6 |
| 12.23 | 10.0 |
| 14.26 | 24.7 |
| 14.81 | 25.4 |
| 15.52 | 53.3 |
| 16.21 | 67.7 |
| 16.81 | 36.3 |
| 18.52 | 79.0 |
| 19.89 | 58.8 |
| 20.62 | 97.4 |
| 21.84 | 99.3 |
| 24.96 | 46.5 |
| 25.94 | 22.3 |

In a further embodiment of the invention, there is provided a process for the preparation of niraparib tosylate Form APO-I, the process comprising mixing together a solid phase of niraparib tosylate and a solid phase of urea for a suitable time to afford the crystalline form.

The process of mixing together solid phases of niraparib tosylate and urea may comprise any method by which the solid phases are intimately contacted throughout, preferably with an input of energy, and may include, for example, mechanochemical methods such as milling, grinding, acoustic resonant mixing, and ultrasound-assisted mixing. Preferably, the mixing comprises milling or grinding.

Preferably, mixing is conducted in the presence of a limited or minimal amount of a suitable solvent such that the solid phases are wetted by the solvent but do not fully dissolve. For example, the mixing preferably comprises 'liquid-assisted grinding' or 'LAG', which comprises mechanical reduction of the particle size of a solid in the presence of a small amount of solvent. Preferably, the suitable solvent is a nitrile solvent. More preferably, the suitable solvent is acetonitrile. The amount of suitable solvent used is preferably between approximately 5 wt % and approximately 20 wt %, more preferably it is between approximately 10 wt % and approximately 15 wt %.

A suitable time for mixing can be optimized taking into consideration factors such as scale, intensity and method of mixing. For example, a suitable time using a liquid-assisted grinding method at a frequency of 25 to 30 Hz is preferably between approximately 0.5 hours and 3 hours on a 1 g scale.

The process may be conducted at any suitable temperature. Preferably, the suitable temperature is between approximately 15° C. and approximately 30° C., more preferably the suitable temperature is between approximately 20° C. and approximately 30° C.

The process may comprise a drying step, if necessary, to ensure reduction of any residual solvent. Drying may be conducted in vacuo, preferably at room temperature.

In another embodiment of the present invention, there is provided a new crystalline form of niraparib tosylate, niraparib tosylate Form APO-II, comprising niraparib tosylate and oxalic acid. Preferably, in niraparib tosylate Form APO-II, the molar ratio of niraparib tosylate to oxalic acid is approximately 1:1.

Niraparib tosylate Form APO-II can be characterized by a PXRD diffractogram comprising, among other peaks, characteristic peaks, expressed in degrees 2θ (±0.2°), at 5.8°, 7.6° and 10.6°. Preferably, the PXRD diffractogram further comprises at least three peaks, expressed in degrees 2θ (±0.2°), selected from the group consisting of 12.8°, 14.2°, 15.2°, 16.7°, 17.3° and 20.9°. More preferably, the PXRD diffractogram further comprises peaks, expressed in degrees 2θ (±0.2°), at 12.8°, 14.2°, 15.2°, 16.7°, 17.3° and 20.9°.

An illustrative PXRD diffractogram of niraparib tosylate Form APO-II, as prepared in Example 2, is shown in FIG. 2. A peak listing, comprising representative peaks from the PXRD diffractogram in FIG. 2, and their relative intensities, is provided in Table 2. Although illustrative of the PXRD diffractogram that is provided for the niraparib tosylate Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of niraparib tosylate Form APO-II from FIG. 2

| Angle (2θ) | Relative intensity (%) |
|---|---|
| 5.82 | 4.9 |
| 7.62 | 29.6 |
| 9.49 | 59.3 |
| 10.59 | 10.0 |
| 12.28 | 15.2 |
| 12.78 | 10.1 |
| 13.16 | 29.3 |
| 14.24 | 55.3 |
| 15.21 | 32.2 |
| 16.21 | 11.0 |
| 16.65 | 22.9 |
| 17.27 | 32.0 |
| 18.33 | 100.0 |
| 19.81 | 44.6 |
| 20.89 | 40.6 |
| 22.18 | 34.7 |
| 23.04 | 56.3 |
| 23.50 | 72.1 |
| 24.83 | 27.3 |
| 25.90 | 34.8 |

In a further embodiment of the invention, there is provided a process for the preparation of niraparib tosylate Form APO-II, the process comprising mixing together a solid phase of niraparib tosylate and a solid phase of oxalic acid for a suitable time to afford the crystalline form.

The process of mixing together solid phases of niraparib tosylate and oxalic acid may comprise any method by which the solid phases are intimately contacted throughout, preferably with an input of energy, and may include, for example, mechanochemical methods such as milling, grinding, acoustic resonant mixing, and ultrasound-assisted mixing. Preferably, the mixing comprises milling or grinding.

Preferably, mixing is conducted in the presence of a limited or minimal amount of a suitable solvent such that the solid phases are wetted by the solvent but do not fully dissolve. For example, the mixing preferably comprises 'liquid-assisted grinding' or 'LAG', which comprises mechanical reduction of the particle size of a solid in the presence of a small amount of solvent. Preferably, the suitable solvent is selected from the group consisting of nitriles, methanol, and ethanol. More preferably, the suitable solvent is methanol. The amount of suitable solvent used is preferably between approximately 5 wt % and approximately 20 wt %, more preferably it is between approximately 10 wt % and approximately 15 wt %.

A suitable time for mixing can be optimized taking into consideration factors such as scale, intensity, and method of mixing. For example, a suitable time using a liquid-assisted grinding method at a frequency of 25 to 30 Hz is preferably between approximately 0.5 hours and 3 hours on a 1 g scale.

The process may be conducted at any suitable temperature. Preferably, the suitable temperature is between approximately 15° C. and approximately 30° C., more preferably the suitable temperature is between approximately 20° C. and approximately 30° C.

The process may comprise a drying step, if necessary, to ensure reduction of any residual solvent. Drying may be conducted in vacuo, preferably at room temperature.

The niraparib tosylate used as a starting material in the processes of the present invention may be any crystalline or amorphous form of niraparib tosylate including, for example, crystalline Form I, II and/or III as described in WO 2018/183354 A1.

In a further embodiment of the invention, there is provided a pharmaceutical composition of a crystalline form of niraparib tosylate comprising niraparib tosylate and urea with one or more pharmaceutically acceptable excipients. In a further embodiment of the invention, there is provided a pharmaceutical composition of a crystalline form of niraparib tosylate comprising niraparib tosylate and oxalic acid with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a capsule. Preferably, the pharmaceutical composition provides a dose of niraparib tosylate that is equivalent to the 100 mg of niraparib free base found in ZEJULA® drug products, as an example of an effective amount. "Effective amount" or "therapeutically effective amount" is meant to describe an amount of compound or a composition of the present invention effective in inhibiting the above-noted diseases and thus producing the desired therapeutic, ameliorative, inhibitory or preventative effect. For example, in some embodiments, a therapeutically effective amount of niraparib tosylate administered to a subject via a solid dosage form is in the range of about 1 mg to about 1000 mg. In some embodiments, a therapeutically effective amount of niraparib tosylate administered to a subject via a solid dosage form is in the range of from about 50 mg to about 300 mg. In some aspects, the solid oral dosage form can be administered one, two, or three times a day (b.i.d). In some embodiments, the amount can be 100 mg dosage of one capsule (dose unit). For example, the dosage regime can be 3×100 mg capsules/day (300 mg daily).

Suitable pharmaceutically acceptable excipients are preferably inert with respect to the crystalline forms of niraparib tosylate of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such as cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents, or glidants may be added as required. Other suitable excipients and the preparation of solid oral dosage forms are well known to a person of skill in the art, and is described generally, for example, in *Remington The Science and Practice of Pharmacy* 21$^{st}$ *Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy* 21$^{st}$ *Edition* (Lippincott Williams & Wilkins: Philadelphia; 2006; Chapter 46).

EXAMPLES

The following non-limiting examples are illustrative of some of the aspects and embodiments of the invention described herein.

The niraparib tosylate used as a starting material in the following examples was consistent with crystalline Form I, which is reported in WO 2018/183354 A1. Other polymorphic forms are equally suitable as starting material, including anhydrous and amorphous forms, when preparing the novel crystalline forms of niraparib tosylate of the present invention.

PXRD Analysis:

PXRD diffractograms were recorded on a Bruker D8 Discover powder X-ray diffractometer (Bruker-AXS, Karlsruhe, Germany). The sample holder was oscillated along X and Y axes during the measurement. The generator was a Incoatec Microfocus Source (IμS) Cu tube (λ=1.54060 Å) with a voltage of 50 kV and current of 1.00 mA, using a divergence slit of 0.5 mm and collimator of 0.5 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1: Preparation of Niraparib Tosylate Form APO-I

Niraparib tosylate (1.00 g) and urea (0.12 g) were added together in a 15 mL stainless steel milling jar. The jar was fitted with a single 12 mm stainless steel ball and was tightly sealed. The solid mixture was milled neat (i.e. no additional solvent added) at room temperature for 10 minutes at 25 Hz using a Retsch Mixer Mill MM 301. Acetonitrile (200 μL) was then added and milling was continued for another 30 minutes at 25 Hz after which the jar was opened and left open for 10 minutes. This cycle of milling in the presence of acetonitrile was repeated twice more, after which the milling jar was opened and the contents removed. The resulting powder was then placed in a vial and dried in vacuo at 30° C. for 2 hours to afford niraparib tosylate Form APO-I as a white solid. $^{1}$H NMR analysis of the solid (DMSO-d6) identified a molar ratio of niraparib tosylate:urea of approximately 1:1. The PXRD diffractogram of a sample prepared by this method is shown in FIG. 1. TGA analysis (25-360° C.@10° C./min; 85 mL/min $N_2$ flow) of the sample showed a weight loss of 2.2% between 37° C. and 121° C., which may be indicative of water loss corresponding with approximately 0.5 mole equivalents.

$^{1}$H-NMR (300 MHz, DMSO-d6): δ=9.31 (s, 1H), 8.87 (d, J=9.8 Hz, 1H), 8.58 (s, 1H), 8.53 (d, J=10.3 Hz, 1H), 8.13-8.00 (m, 4H), 7.93 (s, 1H), 7.52 (t, J=8.3 Hz, 4H), 7.27 (t, J=15.3, 1H), 7.13 (d, J=7.7 Hz, 2H), 5.49 (s, 4H), 3.38-3.32 (m, 2H), 3.13-2.93 (m, 3H), 2.27 (s, 3H) 1.93-1.76 (m, 2H).

Example 2: Preparation of Niraparib Tosylate Form APO-II

Niraparib tosylate (0.50 g) and oxalic acid (0.091 g) were added together in a 15 mL stainless steel milling jar. The jar was fitted with a single 12 mm stainless steel ball and was tightly sealed. The solid mixture was milled neat (i.e. no additional solvent added) at room temperature for 5 minutes at 25 Hz using a Retsch Mixer Mill MM 301. Methanol (100 μL) was then added and milling was continued for another 30 minutes at 25 Hz after which the jar was opened and left open for 10 minutes. Additional methanol (50 μL) was added and milling continued for another 30 minutes at 25 Hz, after which the milling jar was opened and the contents removed. The resulting powder was then placed in a vial and dried in vacuo at 30° C. for 12 hours to afford niraparib tosylate Form APO-II as a white solid. The PXRD diffractogram of a sample prepared by this method is shown in FIG. 2. TGA analysis (25-360° C.@10° C./min; 85 mL/min $N_2$ flow) of the sample showed a weight loss of 4.6% between 37° C. and 115° C., which may be indicative of water loss corresponding with approximately 1.5 mole equivalents.

Example 3: Comparative Intrinsic Dissolution Rate Testing

Intrinsic dissolution rate (IDR) measurements were performed using a Wood apparatus. Samples were prepared by compressing the sample at 1.5 metric tons for 1 minute. A dissolution medium consisting of 900 mL 0.01 N HCl buffer, and rotation speed of 50 rpm was used for each experiment. Results are provided in Table 3.

TABLE 3

Comparative intrinsic dissolution rates for a crystalline form of the invention with the crystalline Form I of niraparib tosylate described in WO 2018/183354 A1

| Form | Intrinsic Dissolution Rate (mg min$^{-1}$ cm$^{-2}$) |
| --- | --- |
| Niraparib tosylate crystalline Form I (400 mg) (Prior Art) | 0.1451 |
| Niraparib tosylate Form APO-II (300 mg) | 0.3110 |

Example 4: Comparative Powder Chargeability Testing

Samples (1 g) were initially placed in a small glass dish inside a desiccator for 30 minutes. The initial electric field of each sample was then measured with a JCI 140 Static Monitor (John Chubb Instrumentation, England) wherein the height of the field meter from top of the glass dish was 2.5 cm. The initial electric field was negligible for each sample. Each sample was then placed in a 20 mL plastic vial and agitated inside of a ball mill (Retsch Mixer Mill MM 301) for 2 hrs at 30 Hz. After the agitation period, each sample was returned to the glass dish and the electric field was measured. The ambient relative humidity during the experiments was 60%. Results are provided in

TABLE 4

Comparative chargeability of a crystalline form of the invention with the crystalline Form I of niraparib tosylate described in WO 2018/183354 A1

| Form | Electric Field After Agitation (kV) |
| --- | --- |
| Niraparib tosylate crystalline Form I (Prior Art) | 0.50 |
| Niraparib tosylate Form APO-1 | 0.16 |

What is claimed is:

1. A crystalline form of niraparib tosylate comprising niraparib tosylate and urea.

2. The crystalline form of claim 1, wherein the molar ratio of niraparib tosylate to urea is between approximately 1:0.75 and approximately 1:1.25.

3. The crystalline form of claim 1, wherein the molar ratio of niraparib tosylate to urea is approximately 1:1.

4. The crystalline form of claim 1, characterized by a PXRD diffractogram comprising peaks, expressed in degrees 2θ (±0.2°), at 5.2°, 6.6° and 8.4°.

5. The crystalline form of claim 4, further comprising at least three peaks in the PXRD diffractogram, expressed in degrees 2θ (±0.2°), selected from the group consisting of: 12.2°, 14.3°, 14.8°, 15.5°, 18.5° and 21.8°.

6. The crystalline form of claim 4, further comprising peaks in the PXRD diffractogram, expressed in degrees 2θ (±0.2°), at 12.2°, 14.3°, 14.8°, 15.5°, 18.5° and 21.8°.

7. The crystalline form of claim 4, providing a PXRD diffractogram comprising peaks in substantially the same positions (±0.2° 2θ) as those shown in FIG. 1.

8. A crystalline form of niraparib tosylate comprising niraparib tosylate and oxalic acid.

9. The crystalline form of claim 8, wherein the molar ratio of niraparib tosylate to oxalic acid is between approximately 1:0.75 and approximately 1:1.25.

10. The crystalline form of claim 8, wherein the molar ratio of niraparib tosylate to oxalic acid is approximately 1:1.

11. The crystalline form of niraparib tosylate of claim 8, characterized by a PXRD diffractogram comprising peaks, expressed in degrees 2θ (±0.2°), at 5.8°, 7.6° and 10.6°.

12. The crystalline form of claim 11, further comprising at least three peaks in the PXRD diffractogram, expressed in degrees 2θ (±0.2°), selected from the group consisting of: 12.8°, 14.2°, 15.2°, 16.7°, 17.3° and 20.9°.

13. The crystalline form of claim 11, further comprising peaks in the PXRD diffractogram, expressed in degrees 2θ (±0.2°), at 12.8°, 14.2°, 15.2°, 16.7°, 17.3° and 20.9°.

14. The crystalline form of claim 11, providing a PXRD diffractogram comprising peaks in substantially the same positions (±0.2° 2θ) as those shown in FIG. 2.

15. A pharmaceutical composition comprising the crystalline form of niraparib tosylate according to claim 4, and one or more pharmaceutically acceptable excipients.

16. The pharmaceutical composition of claim 15, wherein the pharmaceutical composition is a capsule.

17. A method for treating cancer selected from the group consisting of epithelial ovarian, fallopian tube, primary peritoneal and combinations thereof comprising administering an effective amount of the crystalline form of niraparib tosylate according to claim 4.

18. A process for the preparation of the crystalline form of niraparib tosylate according to claim 4, the process comprising mixing together a solid phase of niraparib tosylate and a solid phase of urea for a suitable time to afford the crystalline form of niraparib tosylate.

19. The process of claim 18, wherein the mixing is conducted in the presence of a limited amount of a suitable solvent so as to maintain a solid phase throughout mixing.

20. The process of claim 19, wherein the suitable solvent is acetonitrile.

* * * * *